United States Patent [19]

Odenwälder et al.

[11] Patent Number: 5,306,605
[45] Date of Patent: Apr. 26, 1994

[54] PHOTOGRAPHIC RECORDING MATERIAL

[75] Inventors: Heinrich Odenwälder, Leverkusen; Lothar Rosenhahn, Köln; Thomas Stetzer, Langenfeld, all of Fed. Rep. of Germany

[73] Assignee: AGFA-Gevaert AG, Leverkusen

[21] Appl. No.: 42,585

[22] Filed: Apr. 5, 1993

[30] Foreign Application Priority Data

Apr. 16, 1992 [DE] Fed. Rep. of Germany ....... 4212795

[51] Int. Cl.$^5$ ............................. G03C 7/32; G03C 1/34; G03C 1/42
[52] U.S. Cl. .................................. 430/509; 430/504; 430/506; 430/544; 430/566; 430/614; 430/957; 430/959; 430/379
[58] Field of Search ............... 430/544, 957, 959, 566, 430/506, 509, 504, 614

[56] References Cited

U.S. PATENT DOCUMENTS 4,310,621  1/1982  Odenwalder ................. 430/443
4,524,130  6/1985  Iwasa et al. .................. 430/544

Primary Examiner—Richard L. Schilling
Attorney, Agent, or Firm—Connolly & Hutz

[57] ABSTRACT

A photographic recording material comprising a carrier and at least one photosensitive silver halide emulsion layer, a non-photosensitive layer and optional conventional intermediate and protective layers, characterised in that the photographic recording material (1) contains at least one silver halide emulsion layer having a silver iodide content $\geq 3$ mol % and an average grain diameter $\leq 0.4$ μm, and (2), at least in one layer, contains a compound having the formula I

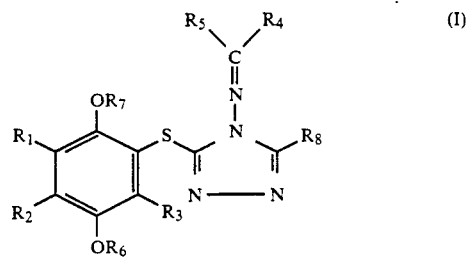

in which $R_1$, $R_2$ and $R_3$ denote hydrogen, an optionally substituted hydrocarbon radical, an optionally substituted alkylthio, alkyloxy or arylthio radical, an optionally substituted amino group, OH or halogen or $R^1$ and $R^2$ together denote the radical for completing a carbocyclic or heterocyclic ring, $R_4$, $R_5$ denote hydrogen, an optionally substituted alkyl or aryl radical, or an optionally substituted heterocyclic radical, $R_6$, $R_7$ denote hydrogen or a radical which can be split off in alkaline solution, and $R_8$ denotes hydrogen, an optionally substituted alkyl or aryl radical, or an optionally substituted alkylthio radical.

The material gives excellent inter-image and edge-effects and has improved sharpness and grain as compared with conventional materials.

8 Claims, No Drawings

PHOTOGRAPHIC RECORDING MATERIAL

The invention relates to a photographic recording material characterised by good inter-image effects and improved sharpness and grain.

As is known, all modern colour photographic recording materials operate on the principle of subtractive colour generation. The general principle of this method of photographic colour recording is as follows; yellow, magenta and cyan dyes are produced in the positive image in such a manner that their concentrations are in inverse ratio to the intensity of the irradiated blue, green and red light.

The production of dyes is based on the fact that during development, as a result of the reduction of silver halide to silver at the illuminated places, developer oxidation products are formed and react with colourless components, called colour-couplers, to form photographic dyes in the layers. Depending on the nature of the colour couplers, yellow photographic dyes are obtained from β-keto anilides, magenta dyes are obtained from pyrazolones and cyan dyes are obtained form α-naphthols or phenols.

The method of substitution and incorporation of the colour couplers in the photographic layer critically influences the absorption of the photographic dyes and consequently influences the colour reproduction. Ideally, the three photographic dyes should absorb in only one third of the spectrum. This is impossible in practice. Overlapping absorption regions and subsidiary absorption in other spectral regions are particularly disadvantageous, since they distort the colour.

To overcome these faults in the past, compounds have been added to the photographic recording material so as to obtain an "inter-image" effect (e.g. U.S. Pat. No. 3,536,487).

The inter-image effect is described in detail inter alia in Hanson et al., Journal of the Optical Society of America, Volume 42, pages 663 to 669 and in A. Thiels, Zeitschrift für Wissenschaftliche Photographie, Photophysik und Photochemie, Volume 47, pages 106 to 118 and pages 246 to 255.

As is also known, inter-image effects can be obtained by incorporating DIR compounds (DIR = development inhibitor releasing) in the layers of a photographic material. DIR compounds can be substances which, by splitting off an inhibitor radical, react with the oxidation product of a colour developer to form a dye (DIR couplers) or substances which release the inhibitor without simultaneously forming a dye. The latter substances are also called DIR compounds in the narrower sense. Released development inhibitors are usually heterocyclic mercapto compounds or derivatives of benzotriazole (see e.g. E. Ranz, Chemie für Labor und Betrieb, Volume 6 (1979), pages 229 to 231).

In colour reversal materials, however, these DIR compounds are of little value in controlling the inter-image and edge-effects, since they become active only in the colour developer and it is very difficult to obtain inhibiting effects in the reverse colour development process.

However, IRD (= inhibitor releasing developer) compounds, e.g. the DIR hydroquinones from DE-A-2 952 280, are active in the first developer (a black-and-white developer) in colour reversal development. Their inhibiting effects can be used to obtain high inter-image and edge-effects.

It has now surprisingly been found that the aforementioned effects can be additionally significantly improved if DIR hydroquinones are used in a photographic material having a special layer structure.

The invention therefore relates to a photographic recording material comprising a carrier and at least one photosensitive silver halide emulsion layer, a non-photosensitive layer and optional conventional intermediate and protective layers, characterised in that the photographic recording material (1) contains at least one silver halide emulsion layer having a silver iodide content $\geq 3$ mol % and an average grain diameter $\leq 0.4$ μm, and (2), at least in one layer, contains a compound having the formula I

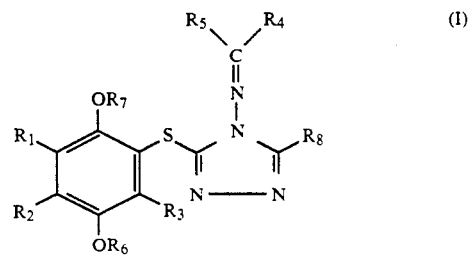

in which $R_1$, $R_2$ and $R_3$ denote hydrogen, an optionally substituted hydrocarbon radical, an optionally substituted alkylthio, alkyloxy or arylthio radical, an optionally substituted amino group, OH or halogen or $R^1$ and $R^2$ together for completing a carbocyclic or heterocyclic ring, $R_4$, $R_5$ denote hydrogen, an optionally substituted alkyl or aryl radical, or an optionally substituted heterocyclic radical, $R_6$, $R_7$ denote hydrogen or a radical which can be split off in alkaline solution, and $R_8$ denotes hydrogen, an optionally substituted alkyl or aryl radical, or an optionally substituted alkylthio radical.

The aforementioned alkyl radicals can more particularly contain up to 20 C atoms. The aforementioned aryl radicals are more particularly phenyl or naphthyl. The heterocyclic radicals preferably contain a 5 to 7-member heterocyclic ring.

Also, at least one of the substituents $R_1$ to $R_3$ can contain a diffusion-fixing radical, preferably a long-chain alkyl radical. Diffusion-fixing radicals are substances for incorporating the compounds according to the invention in diffusion-resistant manner in the hydrophilic colloids conventionally used in photographic materials. To this end it is preferable to use organic radicals usually containing straight-chain or branched aliphatic groups, optionally with carbocyclic or heterocyclic aromatic groups. The aliphatic part of these radicals usually contains 8 to 20 carbon atoms. These radicals are joined to the remaining part of the molecule either directly or indirectly, e.g. via one of the following groups: —CONH—, —SO$_2$NH—, —CO—, —SO$_2$— or —NR—, where R denotes hydrogen or alkyl, —O— or —S—.

In a preferred embodiment the formula I compounds have the following formula II:

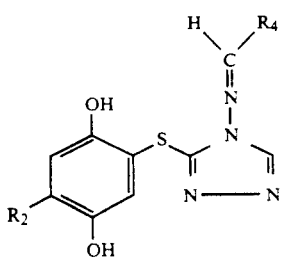

(II)

in which

R$_2$ denotes hydrogen, an optionally substituted alkyl radical, more particularly with 1 to 20 carbon atoms, or an optionally substituted alkylthio radical, and R$_4$ denotes hydrogen or an optionally substituted alkyl, aryl or heterocyclic radical.

Particularly advantageous compounds according to formula II are given in the following Table I.

TABLE 1

| R$_2$ | R$_4$ | Compound |
|---|---|---|
| $-S-C_{16}H_{33}$ | furyl | I-1 |
| $-SCH_2CONH-$ (phenyl with $SO_2NH_2$ and $OC_{16}H_{33}$) | furyl | I-2 |
| $-SC_{12}H_{25}$ | phenyl | I-3 |
| $-SC_{16}H_{33}$ | phenyl | I-4 |
| $-SC_{12}H_{25}$ | furyl | I-5 |
| $-SC_8H_{17}$ | furyl | I-6 |
| $-SC_{16}H_{33}$ | $-\underset{\underset{CH_3}{\mid}}{\overset{\overset{CH_3}{\mid}}{C}}-CH_2-N(CH_3)_2$ | I-7 |
| $-SC_{16}H_{33}$ | 2,5-dimethylfuryl | I-8 |
| $-C_{15}H_{31}$ | furyl | I-9 |
| $-SC_{16}H_{33}$ | benzodioxolyl | I-10 |
| $-SC_{12}H_{25}$ | $-C_6H_4-SO_2NH_2$ | I-11 |

TABLE 1-continued

| R₂ | R₄ | Compound |
|---|---|---|
| −SCH₂CONH− (attached to benzene ring with Cl, NHCO(CH₂)₃−O− bearing 2,4-di-t-C₅H₁₁ phenyl group) | −C₆H₄−OH (para) | I-12 |
| −C₁₅H₃₁ | −C₆H₄−SO₂NH₂ (para) | I-13 |
| −SC₁₆H₃₃ | −C₆H₄−CH₃ (meta) | I-14 |
| −SC₁₂H₂₅ | −C₆H₄−Cl (para) | I-15 |
| −SC₁₂H₂₅ | 2-thienyl | I-16 |

The compounds according to the invention are prepared in known manner, e.g. by adding a heterocyclic thiol to a p-benzoquinone.

By way of example, the manufacture of compound I-1 will now be described.

PREPARATION OF COMPOUND I-1

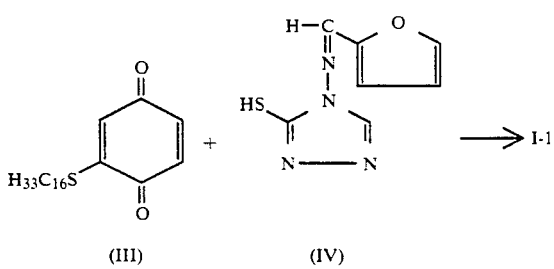

21.6 g of compound III and 11.6 g of compound IV (prepared from 4-amino-5-mercapto-1,2,4-triazole and 2-furan carbaldehyde) were mixed with 300 ml methylene chloride and vigorously agitated for 10 minutes. Next, 11.4 g of p-toluene sulphonic acid monohydrate was added to the suspension. After one and a half hours, the solution was filtered and the filtrate was concentrated in vacuo. The residue was agitated with 200 ml of a mixture of acetonitrile and water (3:1) and the precipitate was suction-filtered and washed first with water and then with acetonitrile.

| Yield: 29.4 g | Melting-point: 132 to 135° C. | |
|---|---|---|
| | Calc.[%] | Found.[%] |
| C | 62.3 | 62.3 |
| H | 7.6 | 7.3 |
| N | 10.0 | 10.1 |

As a rule, the compounds according to the invention are present in the material in a proportion of $10^{-4}$ to $10^{-1}$ mol per mol of silver halide.

The concentration depends on the intended use, the silver halide emulsion used, and whether the compound is in a silver halide emulsion layer or in a non-photosensitive binder layer. The upper limit is usually at concentrations at which colour couplers are also used in photographic layers, but this limit is not critical.

Although the compounds according to the invention can be added to any layer of the photographic material, in a preferred embodiment the compounds are added to a layer not containing any silver halide. In a particularly preferred form of the invention, the compounds are added to a layer disposed between the carrier and the first silver halide emulsion layer.

Alternatively an additional free development inhibitor can be added to the photographic recording material according to the invention. By means of this feature, the properties of the material according to the invention, more particularly the stability in storage, can be additionally and considerably improved, even under hot and moist conditions.

Free development inhibitors for adding to the photographic recording material in another preferred embodiment, can e.g. be mercapto-triazoles having the formula III or mercapto oxadiazoles having the formula IV:

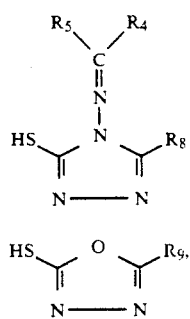
(III)

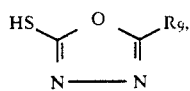
(IV)

$R_4$, $R_5$ denote hydrogen or an optionally substituted alkyl or aryl radical or an optionally substituted heterocyclic radical, $R_8$ denotes hydrogen or an optionally substituted alkyl or aryl radical or an optionally substituted alkylthio radical, and $R_9$ denotes hydrogen or an optionally substituted alkyl or aryl radical or an optionally substituted heterocyclic radical.

Particularly advantageous mercapto triazoles having the formula III are given in Table 2.

TABLE 2

| $R_8$ | $R_5$ | $R_4$ | Compound |
|---|---|---|---|
| H | H | —C₆H₅ (phenyl) | A-1 |
| H | H | —(2-furyl) | A-2 |
| H | H | —(3,4-methylenedioxyphenyl) | A-3 |
| H | H | —(2,5-dimethyl-furyl with CH₃) | A-4 |
| C₂H₅ | H | —C₆H₄—OCH(CH₃)COOCH₃ | A-5 |
| CH₃ | H | —C₆H₄—OH | A-6 |
| H | H | —C(=S)(CH₃)—N=... S—CH₃ | A-7 |
| —SCH₃ | H | —CH(CH₃)₂ | A-8 |
| —S—CH₂—COOC₂H₅ | H | —(2-furyl) | A-9 |

TABLE 2-continued

[Structure: central C=N-N with R5, R4 on the carbon; HS-C and C-R8 attached to the N-N of a 1,2,4-triazole ring (N—N)]

| R8 | R5 | R4 | (aryl/het group) | Compound |
|---|---|---|---|---|
| (phenyl) | CH3 | CH3 | | A-10 |
| H | H | H | 4-(phenyl-CH=N-N(triazole-SH)) | A-11 |
| H | H | H | 4-chlorophenyl | A-12 |
| H | H | H | 4-methoxyphenyl (—OCH3) | A-13 |
| H | H | H | 3-methylphenyl (—CH3) | A-14 |
| H | H | H | 2-thienyl (S) | A-15 |
| H | H | H | 4-pyridyl (N) | A-16 |

Particularly advantageous mercapto oxadiazoles having the formula IV are given in Table 3:

TABLE 3

[Structure: HS—C(=N)—O—C(=N)—R9, 1,3,4-oxadiazole ring N—N]

| R9 | Compound |
|---|---|
| —CH2CH2— linked to second oxadiazole (SH, N—N, O) | B-1 |
| —(CH2)4— linked to second oxadiazole (SH, N—N, O) | B-2 |
| 2-furyl (O) | B-3 |
| 3,4-dichlorophenyl (Cl, Cl) | B-4 |

TABLE 3-continued

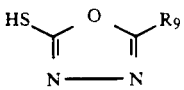

| R9 | Compound |
|---|---|
| 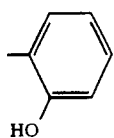 | B-5 |
| 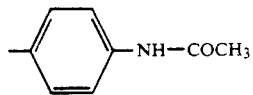 | B-6 |
| 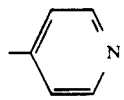 | B-7 |
|  | B-8 |
| 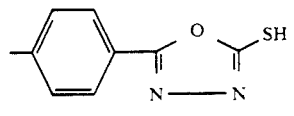 | B-9 |
| 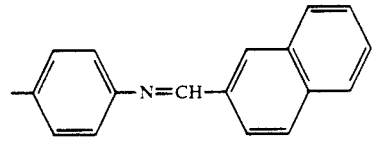 | B-10 |
| 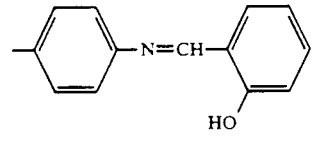 | B-11 |
| 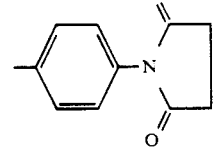 | B-12 |
| —C$_6$H$_{13}$ | B-13 |
| —CH$_2$CH$_2$—S—CH$_2$CH$_2$- ... | B-14 |

The free development inhibitors can be added to any layer of the photographic material, but in a particularly preferred embodiment the compounds are added to a photosensitive silver halide emulsion layer.

Usually the free development inhibitors are present in the material in a proportion of $10^{-4}$ to $10^{-1}$ mol per mol of silver halide.

Preferably the silver halide emulsion layer according to the invention has a silver iodide content of 4 to 6 mol % and an average grain diameter of 0.15 to 0.35 μm.

In a preferred embodiment, the emulsion layer is the less sensitive out of two emulsion layers which are sensitised in the same spectral region.

In another preferred embodiment, the emulsion layer is the medium-sensitive or the least sensitive out of three emulsion layers sensitised in the same region of the spectrum.

In a colour photographic material, the compounds according to the invention are used to obtain excellent inter-image and edge-effects which result in outstanding colour reproduction, detail reproduction and grain. In the case of a black-and-white material, the compounds according to the invention give high sharpness and excellent grain.

A preferred embodiment relates to a colour photographic recording material comprising at least one red-sensitive, at least one green-sensitive and at least one blue-sensitive silver halide emulsion layer which, in the sequence previously given, contain at least one blue-green coupler, at least one purple coupler and at least one yellow coupler.

If the material according to the invention is a colour photographic material, it is preferably a colour negative film, a colour negative paper, a colour reversal film or a colour reversal paper. In the case of black-and-white material, a black-and-white film or a black-and-white paper is preferred.

In a particularly preferred embodiment, the material according to the invention is a colour reversal material.

The silver halides in the layers of silver halide emulsion containing colour couplers or free from colour couplers can be AgBr, AgBrI, AgBrCl, AgBrCll or AgCl.

The silver halide emulsions can operate negatively or directly and positively.

In the case of colour-negative and colour reversal films, silver bromide-iodide emulsions are conventionally used, whereas in the case of colour-negative and colour-reversal paper, it is conventional to use silver chloride-bromide emulsions with a high chloride content, including pure silver chloride emulsions.

The silver halide can consist mainly of compact crystals, which can be regular and cubic or octahedral or have transitional shapes. Preferably however the crystals are twinned, e.g. plate-shaped, the average ratio of diameter to thickness being at least 5:1, the diameter of a grain being defined as the diameter of a circle having an area equal to the projected surface of the grain. Alternatively the layers can have plate-shaped silver halide crystals in which the ratio of diameter to thickness is greater than 5:1, e.g. 12:1 to 30:1.

Alternatively the silver halide grains can have a multi-layered structure, in the simplest case with an inner and an outer grain region (core/shell), with variations in the halide composition and/or other modifications such as doping the individual grain regions. The average grain size of the emulsions is preferably between 0.2 μm and 2.0 μm. The grain size distribution can be homo-dispersed or hetero-dispersed. In addition to silver halide, the emulsions can contain organic silver salts, e.g. silver benzotriazolate or silver behenate.

Two or more kinds of silver halide emulsions can be separately manufactured and used as a mixture.

The photographic emulsions can be prepared by various methods (e.g. P. Glafkides, Chimie et Physique Photographique, Paul Montel, Paris (1967), G. G. Duffin, Photographic Emulsion Chemistry, The Focal Press, London (1966), V. L. Zelikman et al., Making and Coating Photographic Emulsion, The Focal Press, London (1966)), using soluble silver salts and soluble halides.

The silver halides are preferably precipitated in the presence of the binder, e.g. the gelatine, the process being carried out at acid, neutral or alkaline pH, preferably with additional use of silver halide complexing agents, e.g. ammonia, thioethers, imidazole, ammonium thiocyanate or excess halide. The water-soluble silver salts and the halides are either added in succession by the single-jet or simultaneously by the double-jet process or by any combination of the two. Preferably the flow rate of addition is increased, without exceeding the "critical" feed rate at which no new nuclei are produced. The pAg range during precipitation can vary within wide limits, preferably using the "pAg controlled" process, in which a given pAg value is kept constant or a defined pAg profile is maintained during precipitation. As an alternative to the preferred precipitation with an excess of halide, "inverse precipitation" with an excess of silver ions is also possible. Apart from precipitation, the silver halide crystals can also grow as a result of physical ripening (Ostwald ripening) in the presence of excess halide and/or silver halide complexing agents. The growth of the emulsion grains may even occur predominantly through Ostwald ripening) in which case preferably a fine-grained "Lippmann" emulsion is mixed with a more difficultly soluble emulsion and dissolved therein.

Salts or complexes of metals, e.g. Cd, Zn, Pb, Tl, Bi, Ir, Rh or Fe can be present during precipitation and/or physical maturing of the silver halide grains.

Precipitation can also be brought about in the presence of sensitising dyes. Complexing agents and/or dyes can be made inoperative at any desired time, e.g. by altering the pH or by oxidative treatment.

The binder is preferably gelatine, but this can be entirely or partly replaced by other synthetic, semi-synthetic or naturally occurring polymers. Examples of synthetic gelatine replacements are: polyvinyl alcohol, poly-N- vinyl pyrrolidone, polyacrylic amides, polyacrylic acid or derivatives thereof, more particularly copolymers thereof. Natural gelatine substitutes can e.g. be other proteins such as albumin or casein, cellulose, sugar, starch or alginates. Semi-synthetic gelatine substitutes are usually modified natural products, e.g. cellulose derivatives such as hydroxyalkyl cellulose, carboxymethyl cellulose or phthalyl cellulose or gelatine derivatives obtained by reaction with alkylating or acylating agents or by grafting of polymerisable monomers.

The binders should have a sufficient quantity of functional groups, so that sufficiently resistant layers can be obtained by reaction with suitable hardening agents. The functional groups can more particularly be amino groups, or alternatively carboxyl or hydroxyl or active methylene groups.

The preferably-used gelatine can be obtained by acid or alkaline decomposition. This method of producing gelatine is described e.g. in The Science and Technology of Gelatine, published by A. G. Ward and A. Courts, Academic Press 1977, pages 295 ff. The gelatine should have a very low content of photographically active impurities (inert gelatine). Gelatine with high viscosity and low swelling is particularly preferred. The gelatine can be partly or completely oxidised.

After the crystals have formed or at an earlier time, the soluble salts are removed from the emulsion, e.g. by conversion into a paste and washing, by flocculation and washing, by ultrafiltration or by ion exchange.

The photographic emulsions can contain compounds for preventing fogging or for stabilising the photographic operation during production or storage or photographic development.

Azaindenes are particularly suitable, particularly tetra- and penta-azaindenes, more particularly substituted by hydroxyl or amino groups. These compounds have been described e.g. by Birr, Z. Wiss. Phot. 47 (1952), pages 2–58. The anti-fogging agents can also be salts of metals such as mercury or cadmium, aromatic sulphonic or sulphinic acids such as benzenesulphinic acid, or nitrogen-containing heterocyclic substances such as nitrobenzimadazole, nitroindazole, (subst.) benzotriazoles or benzothio-zolium salts. Heterocyclic substances containing mercapto groups are particularly suitable, e.g. mercapto benzothiazoles, mercapto benzimidazoles, mercapto tetrazoles, mercapto thiodiazoles or mercapto pyrimidines, and these mercapto azoles can also contain a water-solubilising group, e.g. a carboxyl group or sulphone group. Other suitable compounds are published in Research Disclosure No. 17643 (1978), Section VI.

The stabilisers can be added to the silver halide emulsions before, during or after ripening. Of course, the compounds can also be added to other photographic layers associated with a silver halide layer.

Mixtures of two or more of the aforementioned compounds can also be used.

The silver halide emulsions are usually chemically ripened, e.g. by action of gold compounds or divalent sulphur compounds.

The photographic emulsion layers or other hydrophilic colloidal layers of the photosensitive material prepared according to the invention can contain surface-active agents for various purposes, such as coating aids or for preventing an electric charge or improving the lubricating properties, emulsifying the dispersion, preventing adhesion or improving the photographic characteristics (e.g. accelerated development, high contrast, sensitisation etc).

The sensitising dyes can be cyanine dyes, more particularly in the following classes:

1. Red Sensitisers

Dicarbocyanines comprising naphthothiazole or benzothiazole basic end groups which can be substituted in the 5 and/or 6 position by halogen, methyl or methoxy, or 9.11-alkylene-bridged, more particularly 9.11-neopentylene thiadicarbocyanines with alkyl or sulphoalkyl substituents on the nitrogen.

2. Green Sensitisers 9-ethyl oxacarbocyanines substituted in the 5 position by chlorine or phenyl and carrying alkyl or sulphoalkyl radicals, preferably sulphoalkyl substituents, on the nitrogen of the benzoxazole groups.

3. Blue Sensitisers

Methine cyanines with benzoxazole, benzothiazole, benzoselenazole, naphthoxazole or naphthothiazole basic end groups, which can be substituted in the 5 and/or 6 position by halogen, methyl or methoxy and carry at least one or preferably two sulphoalkyl substituents on the nitrogen. Apomerocyanines with a rhodanine group are also suitable.

Sensitisers may not be needed if the intrinsic sensitivity of the silver halide, e.g. the blue sensitivity of silver bromide iodides, is sufficient for a given spectral range.

In the case of a colour photographic material, the differently sensitised emulsion layers are associated with non-diffusing monomeric or polymeric colour couplers, which can be in the same layer or in a neighbouring layer. Usually blue-green couplers are associated with the red-sensitive layers, purple couplers with the green-sensitive layers and yellow couplers with the blue-sensitive layers.

Colour couplers for producing the cyan component colour image are usually phenol or o-naphthol-type couplers.

Colour couplers for producing the magenta component colour image are usually 5-pyrazolone or indazolone-type couplers or pyrazoloazoles.

Colour couplers for producing the yellow component colour image usually have an open-chain keto-methylene grouping, more particularly of α-acylacetamide type. α-benzoyl acetanilide couplers and o-pivaloyl acetanilide couplers are suitable examples.

The colour couplers can be 4-equivalent couplers or 2-equivalent couplers. The latter are derived from 4-equivalent couplers in that, at the coupling place, they contain a substituent which is split off during coupling.

The couplers usually contain a ballast radical, to prevent diffusion inside the material, i.e. either inside a layer or from one layer to another. High-molecular couplers can be used instead of couplers with a ballast radical.

Suitable colour couplers or references describing them can be found e.g. in Research Disclosure 17 643 (1978), Chapter VII.

High-molecular colour couplers are described e.g. in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284 or U.S. Pat. No. 4,080,211. High-molecular colour couplers are usually produced by polymerisation of ethylenically unsaturated monomeric colour couplers. Alternatively they can be obtained by polyaddition or polycondensation.

The material can contain other compounds capable of liberating a photographically active substance, e.g. a development inhibitor, a development accelerator, a bleaching accelerator, a developer or a fogging agent.

The compounds for splitting off a development inhibitor can e.g. be DIR couplers (see e.g. Research Disclosure 17 643 (1978) Chapter VII F) or IRD compounds (see e.g. U.S. Pat. No. 4,684,604 and DE-A-31 45 640).

The compounds for splitting off a development accelerator or a fogging agent can e.g. be DAR or FAR couplers (see e.g. DE-A-25 34 466, 34 41 823 and EP-A-0 147 765).

Compounds splitting off a bleaching accelerator can e.g. be BAR couplers (see e.g. EP-A-0 193 389).

The couplers or other compounds can be incorporated in silver halide emulsion layers by first preparing a solution, dispersion or emulsion of the compound in question and then adding it to the solution for casting the respective layer. The choice of a suitable solvent or dispersing agent depends on the solubility of the compound.

Methods of incorporating substantially water-insoluble compounds by grinding are described e.g. in DE-A-26 09 741 and DE-A-26 09 742.

Hydrophobic compounds can also be incorporated in the casting solution by using high-boiling solvents or "oil-forming agents". Corresponding methods are described e.g. in U.S. Pat. Nos. 2,322,027, 2,801,170, 2,801,171 and EP-A-0 043 037.

Instead of high-boiling solvents, oligomers or polymers, i.e. "polymeric oil-forming agents", may be used.

The compounds can also be introduced in the form of charged latices into the casting solution. See e.g. DE-A-25 41 230, DE-A-25 41 274, DE-A-28 35 856, EP-A-0 014 921, EP-A-0 069 671, EP-A-0 130 115 or U.S. Pat. No. 4,291,113.

Anionic water-soluble compounds (e.g. dyes) can also be incorporated in diffusion-resistant manner by using cationic polymers, i.e. "mordant" polymers.

The oil-forming agents can be e.g. phthalic acid alkyl esters, phosphonic acid esters, phosphoric acid esters, citric acid esters, benzoic acid esters, amides, fatty acid esters, trimesic acid esters, alcohols, phenols, aniline derivatives or hydrocarbons.

The oil-forming agents can e.g. be dibutyl phthalate, dicyclohexyl phthalate, di-2-ethyl hexyl phthalate, decyl phthalate, triphenyl phosphate, tricresyl phosphate, 2-ethyl hexyl diphenyl phosphate, tricyclohexyl phosphate, tri-2-ethyl hexyl phosphate, tridecyl phosphate, tributoxyethyl phosphate, trichloropropyl phosphate, di-2-ethyl hexyl phenyl phosphate, 2-ethyl hexyl benzoate, dodecyl benzoate, 2-ethyl hexyl-p-hydroxybenzoate, diethyl dodecanamide, N-tetradecyl pyrrolidone, isostearyl alcohol, 2,4-di-tert.-amyl phenol, dioctyl acetate, glycerol tributyrate, isostearyl lactate, trioctyl citrate, N,N-dibutyl-2-butoxy-5-tert.-octyl aniline, paraffin, dodecyl benzene or diisopropyl naphthalene.

The photographic material can also contain UV-absorbing compounds, optical brighteners, spacers, filter dyes, formaline trapping agents, light-excluding agents, antioxidising agents, $D_{Min}$ dyes, additives for improving the dye, coupler and white stability or reducing the colour fog, plasticisers (latices), biocides and other substances.

The UV-absorbing compounds are designed on the one hand to protect the photographic dyes from bleaching by high-UV daylight, and on the other hand act as filter dyes which absorb the UV light in daylight during illumination and thus improve the colour reproduction of a film. Usually the compounds used for the two purposes have different structures. The following are examples: aryl-substituted benzotriazole compounds (U.S. Pat. No. 3,533,794), 4-thiazolidone compounds (U.S. Pat. Nos. 3,314,794 and 3,352,681), benzophenone compounds (JP-A-2784/71), cinnamic acid ester compounds (U.S. Pat. Nos. 3,705,805 and 3,707,375), butadiene compounds (U.S. Pat. No. 4,045,229) or benzoxazole compounds (U.S. Pat. No. 3,700,455).

In addition, ultraviolet-absorbing couplers (e.g. naphthol-type cyan couplers) and ultraviolet-absorbing polymers can also be used. These ultraviolet-absorbing substances can be fixed in a special layer by mordanting.

Filter dyes suitable for visible light include oxanol dyes, hemioxonol dyes, styryl dyes, merocyanine dyes, cyanine dyes and azo dyes. Out of these dyes, oxonol dyes, hemioxonol dyes and merocyanine dyes are particularly advantageous.

Suitable optical brighteners are described e.g. in Research Disclosure 17 643 (December, 1978), Chapter V, in U.S. Pat. Nos. 2,632,701 and 3,269,840 and in GB-A-852 075 and 1 319 763.

Some binder layers, more particularly the layer most remote from the carrier, or occasionally intermediate layers, particularly when furthest from the carrier during manufacture, can contain inorganic or organic photographically inert particles, e.g. as dulling agents or as spacers (DE-A-33 31 542, DE-A-34 24 893, Research Disclosure 17 643, (December, 1978), Chapter XVI.

The average particle diameter of the spacers is more particularly in the range from 0.2 to 10 μm. The spacers are insoluble in water and can be soluble or insoluble in alkali; usually the alkali-soluble substances are removed from the photographic material in the alkaline development bath. The polymers can e.g. be polymethyl methacrylate, copolymers of acrylic acid and methyl methacrylate or hydroxypropyl methyl cellulose hexahydrophthalate.

Additives for improving the dye, coupler and white stability and reducing the colour fog (Research Disclosure 17 643/1978, Chapter VII) can belong to the following chemical classes: hydroquinones, 6-hydroxychromanes, 5-hydroxycumaranes, spirochromanes, spiroindanes, p-alkoxyphenols, sterically hindered phenols, gallic acid derivatives, methylene dioxybenzenes, aminophenols, sterically hindered amines, derivatives comprising etherified or aesterified phenolic hydroxyl groups, or metal complexes.

Compounds having both a sterically hindered amino partial structure and a sterically hindered phenol partial structure in the same molecule (U.S. Pat. No. 4,268,593) are particularly efficient at preventing damage (impairment or decomposition) to yellow colour-forming agents as a result of evolution of heat, moisture and light. To prevent damage (impairment or decomposition) of purple-red colour-forming agents, more particularly damage (impairment or decomposition) resulting from action of light, it is particularly efficient to use spiroindanes (JP-A-159 644/81) or chromanes substituted by hydroquinone diethers or monoethers (JP-A-89 835/80).

The layers of photographic material can be hardened with the usual substances, e.g. formaldehyde, glutaraldehyde or similar aldehyde compounds, diacetyl, cyclopentadione or similar ketone compounds, bis-(2-chloroethyl) urea), 2-hydroxy-4,6-dichloro-1,3,5-triazine and other compounds containing reactive halogen (U.S. Pat. Nos. 3,288,775, 2,732,303, GB-A-974 723 and GB-A-1 167 207), divinyl sulphone compounds, 5-acetyl-1,3-diacryloyl hexahydro-1,3,5-triazine and other compounds containing a reactive olefin bond (U.S. Pat. Nos. 3,635,718, 3,232,763 and GB-A-994 869); N-hydroxymethyl phthalimide and other N-methylol compounds (U.S. Pat. Nos. 2,732,316 and 2,586,168); isocyanates (U.S. Pat. No. 3,103,437); aziridine compounds (U.S. Pat. Nos. 3,017,280 and 2,983,611); acid derivatives (U.S. Pat. Nos. 2,725,294 and 2,725,295); carbodiimide-type compounds (U.S. Pat. No. 3,100,704); carbamoyl pyridinium salts (DE-A-22 25 230 and DE-A-24 39 551); carbamoyl oxypyridinium compounds (DE-A-24 08 814); compounds containing a phosphorus-halogen bond (JP-A-113 929/83); N-carbonyl oximide compounds (JP-A-43353/81); N-sulphonyl oximido compounds (U.S. Pat. No. 4,111,926), dihydroquinoline compounds (U.S. Pat. No. 4,013,468); 2-sulphonyl oxypyridinium salts (JP-A-110 762/81); formamidinium salts (EP-A-0 162 308), compounds containing two or more N-acyloximino groups (U.S. Pat. No. 4,052,373), epoxy compounds (U.S. Pat. No. 3,091,537), isoxasole-type compounds (U.S. Pat. Nos. 3,321,313 and 3,543,292); halogen carboxyaldehydes such as mucochloric acid; dioxan derivatives such as dihydroxy dioxan and di-chlorodioxan; or inorganic hardeners such as chrome alum or zirconium sulphate.

Hardening can be brought about in known manner by adding the hardening agent to the solution for casting the layer to be hardened, or alternatively the layer to be hardened can be covered with a layer containing a diffusible hardening agent.

The aforementioned classes include slow-acting and quick-acting hardening agents and "immediate" hardening agents, which are particularly advantageous. Immediate hardening agents are compounds which cross-link suitable binders so that immediately after casting, or not later than 24 hours, preferably not later than 8 hours, hardening has advanced sufficiently to prevent the cross-linking reaction from causing any change in sensitometry or swelling of the composite layer. "Swelling" means the difference between the thickness of the wet layer and the thickness of the dry layer during treatment of the film with water (Photogr. Sci., Eng. 8 (1964), 275; photogr. Sci. Eng. (1972), 449).

These hardening agents, which react very quickly with gelatine, are e.g. carbamoyl pyridinium salts which can react with free carboxyl groups on gelatine, so that the free carboxyl groups react with free amino groups on the gelatine to form peptide bonds and cross-link the gelatine.

Some diffusible hardening agents have a similar hardening effect on all layers in a composite layer. Other low-molecular or high-molecular hardening agents do not diffuse and their action is limited to one layer. These can particularly strongly cross-link individual layers, e.g. the protective layer. This is important if the silver halide layer hardens only slightly owing to the increased covering power of the silver, and if the protective layer is designed to improve the mechanical properties (EP-A-0 114 699).

The black-and-white photographic materials according to the invention are usually processed by developing, fixing and washing or stabilising without subsequent washing. In the case of reverse development, the process is preceded by a first development followed by a bleaching step and diffuse secondary illumination or chemical fogging. Reducing agents such as phenols, phenol amines and pyrazolinones are used as the developer substances. Hydroquinone, metol and phenidone are examples of particularly suitable substances for black-and-white photography.

The colour photographic materials according to the invention are usually processed by developing, bleaching, fixing and washing or stabilising without subsequent washing, bleaching and fixing being optionally combined in a single processing step. In reverse development, colour development is preceded by a first development using a developer which does not form a dye with the couplers, and by using diffuse secondary illumination or chemical fogging.

The colour-developing compound can be any developing compounds which, in the form of their oxidation product, are capable of reacting with colour couplers to form azomethine or indophenol dyes. The following colour-developing compounds are suitable: aromatic p-phenylene diamine-type compounds containing at least one primary amino group e.g. N,N-dialkyl-p-phenylene diamines such as N,N-diethyl-p-phenylene diamine, 1-(N-ethyl-N-methanesulphone amidoethyl)-3-methyl-p-phenylene diamine, 1-(N-ethyl-N-hydroxyethyl)-3-methyl-p-phenylene diamine and 1-(N-ethyl-N-methoxyethyl)-3-methyl-p-phenylene diamine. Other useful colour developers are described e.g. in J. Amer. Chem. Soc. 73, 3106 (1951) and G. Haist, Modern Photographic Processing, 1979, John Wiley & Sons, New York, pages 545 ff.

The colour development can be followed by an acid stop bath or washing.

Usually the material is bleached and fixed after colour development. The bleaching agents can e.g. be Fe(III) salts or Fe(III) complex salts such as ferricyanides, dichromates or water-soluble cobalt complexes. It is particularly preferable to use iron-(III) complexes of aminopolycarboxylic acids, more particularly e.g. ethylene diamine tetraacetic acid, propylene diamine tetraacetic acid, diethylene triamine pentaacetic acid, nitrilotriacetic acid, iminodiacetic acid, N-hyroxyethyl ethylene diamine triacetic acid, alkyl iminodicarboxylic acids and corresponding phosphonic acids. Persulphates and peroxides, e.g. hydrogen peroxide, are other suitable bleaching agents.

The bleaching or other mixing bath is usually followed by washing, either in counter-current or in a number of tanks individually supplied with water.

Good results can be obtained by using an immediately following final bath containing little or no formaldehyde.

Alternatively washing can be completely replaced by a stabilising bath, usually in counter-current. When formaldehyde is added, the stabilising bath can also serve as a final bath.

EXAMPLE 1

Recording Material 1.1

The following layers were successively applied to a cellulose triacetate carrier coated with an adhesive layer

| 1st layer | 0.66 g/m² |
| Gelatine | |
| 2nd layer (red-sensitive layer) | |
| Red-sensitised silver halide emulsion | |
| Silver (as AgNO₃) | 2.20 g/m² |
| Coupler C-1 | 1.76 g/m² |
| Gelatine | 2.00 g/m² |
| Tricresyl phosphate (TCF) | 0.88 g/m² |
| 3rd layer (intermediate layer) | |
| Gelatine | 1.90 g/m² |
| Compound S | 0.24 g/m² |
| TCP | 0.12 g/m² |
| 4th layer (green-sensitive layer) | |
| Green-sensitised silver halide emulsion | |
| Silver (as AgNO₃) | 2.20 g/m² |
| Coupler C-3 | 1.32 g/m² |
| Gelatine | 1.76 g/m² |
| TCF | 0.66 g/m² |
| 5th layer (protective layer) | |
| Gelatine | 1.30 g/m² |
| Hardening agent H | 1.16 g/m² |

The exact structure of the recording materials 1.1 to 1.20 and the test measurements are given in Table 4.

TABLE 4

| No. | Compound [μmol/m²] layer 1 | 2 | 4 | Emulsion layer 2 | 4 | Edge-effect $\delta D(D = 1.0)$ cyan | yellow | Inter-image effect $\delta E(D = 0.5)$ Red | Green | |
|---|---|---|---|---|---|---|---|---|---|---|
| 1.1 | — | — | — | A | A | −0.39 | −0.29 | 0.0 | −0.2 | Comparison |
| 1.2 | — | — | — | B | A | −0.26 | −0.40 | 1.0 | 1.0 | Comparison |
| 1.3 | — | — | — | C | C | −0.03 | 0.01 | 0.0 | −0.8 | Comparison |
| 1.4 | — | — | — | B | C | −0.04 | 0.03 | 0.0 | −0.8 | Comparison |
| 1.5 | — | — | — | B | B | −0.11 | −0.20 | 0.4 | −0.5 | Comparison |
| 1.6 | I-1 40 | — | — | A | A | −0.55 | −0.28 | 0.9 | −0.2 | Comparison |
| 1.7 | I-1 40 | — | — | B | A | −0.68 | −0.61 | 1.0 | 2.0 | |
| 1.8 | I-1 40 | — | — | C | C | −0.30 | −0.27 | −0.2 | −0.2 | Comparison |
| 1.9 | I-1 40 | — | — | B | C | −0.62 | −0.25 | 0.5 | 0.0 | |
| 1.10 | I-1 40 | — | — | B | B | −0.66 | −0.62 | 2.0 | 2.5 | |
| 1.11 | — | I-1 30 | — | B | B | −0.73 | −0.53 | 3.0 | 1.5 | |
| 1.12 | — | I-2 30 | — | B | B | −0.55 | −0.32 | 2.0 | 1.2 | |
| 1.13 | — | V 30 | — | B | B | −0.35 | −0.30 | 0.5 | 0.5 | Comparison |
| 1.14 | — | I-1 30 | I-1 30 | B | B | −0.59 | −0.67 | 3.2 | 3.0 | |
| 1.15 | — | I-3 30 | I-3 30 | B | B | −0.62 | −0.59 | 4.0 | 1.0 | |
| 1.16 | — | I-4 30 | I-4 30 | B | B | −0.51 | −0.53 | 3.5 | 1.5 | |
| 1.17 | — | I-5 30 | I-5 30 | B | B | −0.73 | −0.78 | 2.0 | 2.0 | |
| 1.18 | — | I-6 30 | I-6 30 | B | B | −0.78 | −0.70 | 3.5 | 4.0 | |
| 1.19 | I-1 27 A-2 13 | — | — | B | B | −0.71 | −0.69 | 2.5 | 2.0 | |
| 1.20 | I-1 13 A-2 | — | — | B | B | −0.76 | −0.73 | 2.5 | 2.0 | |

TABLE 4-continued

| | Compound [μmol/m²] layer | | | Emulsion layer | | Edge-effect δD(D = 1.0) | | Inter-image effect δE(D = 0.5) | |
|---|---|---|---|---|---|---|---|---|---|
| No. | 1 | 2 | 4 | 2 | 4 | cyan | yellow | Red | Green |
| 27 | | | | | | | | | |

Emulsion A: Average grain diameter 0.22 μm, 99 mol % bromide, 1 mol % iodide

Emulsion B: Average grain diameter 0.22 μm, 94 mol % bromide, 6 mol % iodide

Emulsion C: Average grain diameter 0.64 μm, 95 mol % bromide, 5 mol % iodide.

Samples of the resulting materials were illuminated and subjected to colour reversal development as described in "Manual for PROCESSING Kodak Ektachrome Film using Process E7", Eastman Kodak Company, 1977 (compare Kodak Publication No. Z-119).

The edge-effect is the difference be(ween the microdensity (gap width 30 μm) and the macro-density of reverse-developed samples with macro-density=1, as described in T. H. James, The Theory of the Photographic Process, 4th edition, Macmillan Publishing Co., Inc., page 611 (1977).

The inter-image effects (red) is the difference in sensitivity at D=0.5 between the red-sensitive layer in selective red illumination and in additive red+green illumination, in the case where the red and green sensitivity under additive illumination are the same. Similar remarks apply to the green inter-image effect.

As Table 4 shows, the substances according to the invention in conjunction with the emulsions according to the invention considerably intensify the edge and interimage effect.

EXAMPLE 2

Recording Material 2.1

The following layers were successively applied to a cellulose triacetate carrier coated with an adhesive layer.

| 1st layer (anti-halo layer) | |
|---|---|
| Black colloidal silver sol | 0.25 g/m² |
| Gelatine | 1.60 g/m² |
| UV absorber | 0.24 g/m² |
| 2nd layer (intermediate layer) | |
| Gelatine | 0.64 g/m² |
| 3rd layer (intermediate layer) | |
| Gelatine | 0.60 g/m² |
| 4th layer (first red-sensitive layer) | |
| Red-sensitised silver halide emulsion (average grain diameter 0.25 μm, 97.5 mol % bromide, 2.5 mol % iodide) = emulsion D | |
| Silver (as AgNO₃) | 0.95 g/m² |
| Coupler C-1 | 0.25 g/m² |
| Gelatine | 0.60 g/m² |
| TCP | 0.12 g/m² |
| 5th layer (second red-sensitive layer) | |
| Red-sensitised silver halide emulsion (Average grain diameter 0.43 μm, 97 mol % bromide, 3 mol % iodide) | |
| Silver (as AgNO₃) | 2.40 g/m² |
| Coupler C-1 | 1.54 g/m² |
| Gelatine | 2.58 g/m² |
| TCP | 0.78 g/m² |
| 6th layer (intermediate layer) | |
| Gelatine | 1.78 g/m² |
| Compound S | 0.24 g/m² |
| TCP | 0.12 g/m² |
| 7th layer (first green-sensitive layer) | |
| Green-sensitised silver halide emulsion (average grain diameter 0.25 μm, 98.25 mol % bromide, 1.75 mol % iodide) = emulsion E | |
| Silver (as AgNO₃) | 1.25 g/m² |
| Coupler C-2 | 0.38 g/m² |
| Gelatine | 1.30 g/m² |
| TCP | 0.32 g/m² |
| 8th layer (second green-sensitive layer) | |
| Green-sensitised silver halide emulsion Average grain diameter 0.42 μm, 98.5 mol % bromide, 5 mol % iodide) | |
| Silver (as AgNO₃) | 1.65 g/m² |
| Coupler C-2 | 1.00 g/m² |
| Gelatine | 2.65 g/m² |
| TCP | 1.00 g/m² |
| 9th layer (intermediate layer) | |
| Gelatine | 0.70 g/m² |
| Compound S | 0.10 g/m² |
| TCP | 0.05 g/m² |
| 10th layer (filter yellow layer) | |
| Yellow colloidal silver sol | |
| Silver (as AgNO₃) | 0.19 g/m² |
| Gelatine | 0.75 g/m² |
| 11th layer (intermediate layer) | |
| Gelatine | 0.50 g/m² |
| 12th layer (first blue-sensitive layer) | |
| Blue-sensitised silver halide emulsion (average grain diameter 0.50 μm, 96 mol % bromide, 4 mol % iodide) | |
| Silver (as AgNO₃) | 0.65 g/m² |
| Coupler C-3 | 0.70 g/m² |
| Gelatine | 1.00 g/m² |
| TCP | 0.35 g/m² |
| 13th layer (second blue-sensitive layer) | |
| Blue-sensitised silver halide emulsion (Average grain diameter 0.70 μm, 95 mol % bromide, 5 mol % iodide) | |
| Silver (as AgNO₃) | 1.05 g/m² |
| Coupler C-3 | 1.05 g/m² |
| Gelatine | 2.10 g/m² |
| TCP | 0.53 g/m² |
| 14th layer (intermediate layer) | |
| Compound S | 0.60 g/m² |
| Gelatine | 2.56 g/m² |
| TCP | 0.02 g/m² |
| UV absorber | 0.55 g/m² |
| 15th layer (intermediate layer) | |
| Lippmann-type silver halide emulsion (Average grain diameter 0.15 μm, 96 mol % bromide, 4 mol % iodide) | |
| Silver (as AgNO₃) | 0.33 g/m² |
| Gelatine | 0.60 g/m² |
| 16th layer (protective layer) | |
| Hardening agent H | 0.81 g/m² |
| Gelatine | 0.80 g/m² |

The structure of the recording materials 2.2 to 2.9 and the test results are given in Table 5.

TABLE 5

| | Compound [μmol/m²] layer | | | Emulsion layer | | Edge-effect δD(D = 1.0) | | Inter-image effect δE(D = 1.5) | | | Grain *10³ $\sigma_D$(D = 1.0) | | Sharpness [%] 10 lin/mm | |
|---|---|---|---|---|---|---|---|---|---|---|---|---|---|---|
| No. | 3 | 4 | 7 | 4 | 7 | cyan | magenta | Red | Green | Blue | cyan | magenta | cyan | magenta |
| 2.1 | — | — | — | D | E | −0.30 | −0.34 | −0.6 | 0.1 | −0.3 | 26 | 22 | 69 | 88 |

TABLE 5-continued

| No. | Compound [μmol/m²] layer 3 | 4 | 7 | Emulsion layer 4 | 7 | Edge-effect δD(D = 1.0) cyan | magenta | Inter-image effect δE(D = 1.5) Red | Green | Blue | Grain *10³ σ_D(D = 1.0) cyan | magenta | Sharpness [%] 10 lin/mm cyan | magenta |
|---|---|---|---|---|---|---|---|---|---|---|---|---|---|---|
| 2.2 | I-1 30 | — | — | D | E | −0.44 | −0.42 | −0.3 | −0.1 | −0.3 | 18 | 20 | 86 | 96 |
| 2.3 | — | — | — | F | F | −0.34 | −0.23 | 0.2 | −0.8 | −0.9 | 33 | 30 | 88 | 96 |
| 2.4 | I-1 30 | — | — | F | F | −0.59 | −0.53 | 2.0 | 1.0 | −0.5 | 24 | 25 | 95 | 105 |
| 2.5 | I-1 40 | — | — | F | F | −0.62 | −0.62 | 3.7 | 1.4 | −0.5 | 22 | 24 | 98 | 110 |
| 2.6 | I-2 35 | — | — | F | F | −0.66 | −0.63 | 4.1 | 2.0 | −1.0 | 23 | 23 | 99 | 110 |
| 2.7 | — | I-1 10 | I-1 10 | F | F | −0.59 | −0.50 | 1.5 | 0.5 | −0.9 | 25 | 25 | 95 | 105 |
| 2.8 | I-1 40 | — | — | F | G | −0.68 | −0.60 | 3.2 | 0.0 | −1.0 | 22 | 22 | 85 | 105 |
| 2.9 | I-1 20 A-2 50 | — | — | F | G | −0.65 | −0.62 | 0.9 | 0.1 | −1.0 | 24 | 21 | 86 | 104 |

Emulsion F: Average grain diameter 0.34 μm, 96 mol % bromide, 4 mol % iodide
Emulsion G: Average grain diameter 0.25 μm, 97.5 mol % bromide, 2.5 mol % iodide The edge-effect was determined as described in Example 1. The red inter-image effect is the difference in sensitivity at D=1.5 in the red-sensitive layer between selective red illumination and white illumination (obtained by additive red+green+blue illumination). Corresponding remarks apply to the green and blue interimage effects.

The grain is the standard deviation $\sigma_D$, measured at macrodensity 1.0, of a micro-densitometer track s described in T. H. James, The Theory of the Photographic Process, 4th edition, Macmillan Publishing Co., Inc., page 618 (1977) (test conditions: parallel light, test diaphragm 28.9 μm). The sharpness (MTF) was determined as described in T. H. James, The Theory of the Photographic Process, 4th Edition, Macmillan Publishing Co., Inc., page 604 (1977).

As Table 5 shows, the addition according to the invention in conjunction with emulsion F produced a marked improvement in the edge-effect, inter-image effect, grain and sharpness.

Table 6 shows the colour change in the recording materials 2.8 and 2.9 after three weeks, storage at 40° C. and 50% relative air humidity. As can be seen, the stability of the material according to the invention and under the given storage conditions was considerably improved by adding a free development inhibitor.

TABLE 6

| No. | Compounds [μmol/m²] layer 3 | 4 | 7 | Emulsion layer 4 | 7 | δD yellow δD cyan (Dmagenta = 0.4) | | δD yellow δD cyan (Dmagenta = 0.6) | | δD yellow δD cyan (Dmagenta = 1.0) | | δD yellow δD cyan (Dmagenta = 2.0) | |
|---|---|---|---|---|---|---|---|---|---|---|---|---|---|
| 2.8 | I-1 40 | — | — | F | G | −2 | −4 | −5 | −7 | −10 | −9 | −5 | −9 |
| 2.9 | I-1 20 A-2 50 | — | — | F | G | −2 | 2 | −5 | 2 | −8 | −1 | −1 | −2 |

δD yellow = Change in the difference (yellow density - magenta density) at the magenta densities 0.4; 0.6; 1.0 or 2.0 during the aforementioned storage.
δD cyan = Change in difference (cyan density - magenta density) at the magenta densities 0.4; 0.6; 1.0 or 2.0 during the aforementioned storage.

The components used have the following formulae:

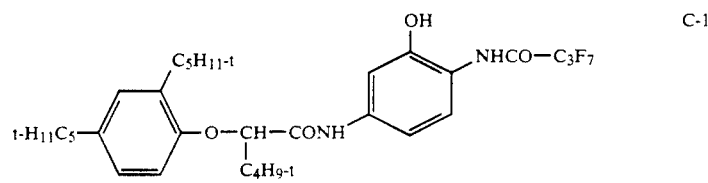

C-1

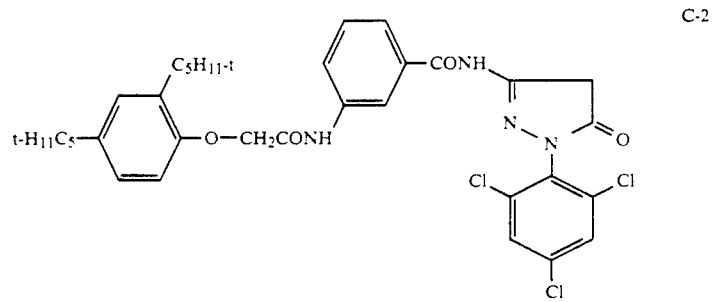

C-2

-continued

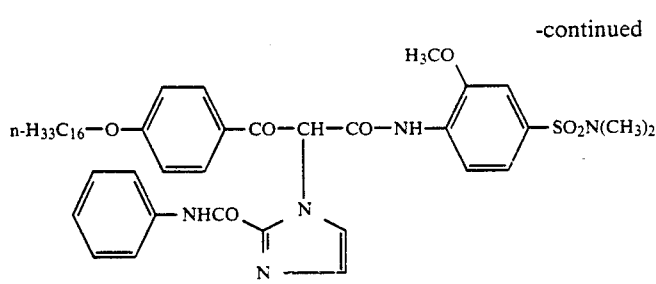 C-3

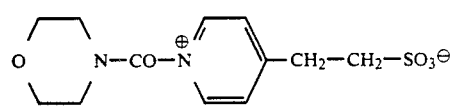 H

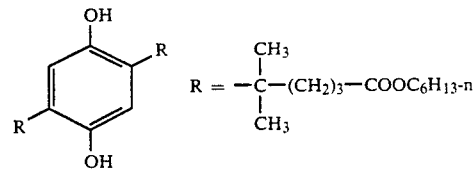 S

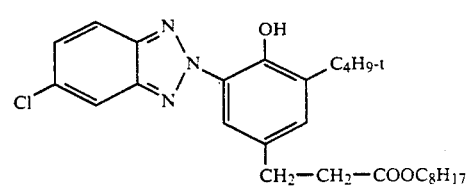 UV

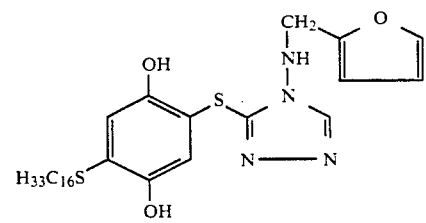 V

We claim:

1. A photographic recording material comprising a carrier and at least one photosensitive silver halide emulsion layer, a non-photosensitive layer and optional intermediate and protective layers, characterised in that the photographic recording material (1) contains at least one silver halide emulsion layer having a silver iodide content $\geq 3$ mol % and an average grain diameter $\leq 0.4$ μm, and (2), at least in one layer, contains a compound having the formula I

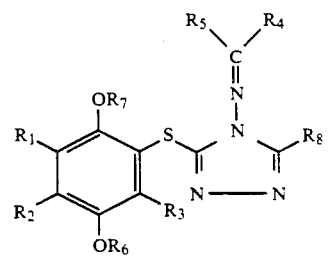 (I)

in which $R_1$, $R_2$ and $R_3$ denote hydrogen, an optionally substituted hydrocarbon radical, an optionally substituted alkylthio, alkyloxy or arylthio radical, an optionally substituted amino group, OH or halogen or $R^1$ and $R^2$ together denote the radical for completing a carbocyclic or heterocyclic ring, $R_4$, $R_5$ denote hydrogen, an optionally substituted alkyl or aryl radical, or an optionally substituted heterocyclic radical, $R_6$, $R_7$ denote hydrogen or a radical which can be split off in alkaline solution, and $R_8$ denotes hydrogen, an optionally substituted alkyl or aryl radical, or an optionally substituted alkylthio radical.

2. A photographic recording material according to claim 1, characterised in that the compound I is in a layer which does not contain silver halide.

3. A photographic recording material according to claim 1, characterised in that it contains the compound I in a layer between the carrier and the first silver halide emulsion layer.

4. A photographic recording material according to claim 1, characterised in that it additionally contains a free development inhibitor.

5. A photographic recording material according to claim 1, characterised in that the silver halide emulsion layer has a silver iodide content of 4 to 6 mol % and an average grain diameter of 0.15 to 0.35 μm.

6. A photographic recording material according to claim 1, containing at least two photosensitive silver halide emulsion layers sensitized in the same spectral region and differing in sensitivity, characterised in that the emulsion according to claim 1 is disposed in the less sensitive layer.

7. A photographic recording material according to claim 1, containing at least three photosensitive silver halide emulsion layers which are sensitized in the same spectral region and differ in sensitivity, characterised in that the emulsion according to claim 1 is disposed in the emulsion layer of medium sensitivity or in the emulsion layer having the lowest sensitivity.

8. A photographic recording material according to claim 1, characterised in that it is a colour reversal material.

* * * * *

UNITED STATES PATENT AND TRADEMARK OFFICE
CERTIFICATE OF CORRECTION

PATENT NO. : 5,306,605
DATED : April 26, 1994
INVENTOR(S) : Heinrich Odenwalder, et al.

It is certified that error appears in the above-indentified patent and that said Letters Patent is hereby corrected as shown below:

Column 20, line 17, "TCF" should read --TCP--.

Column 20, line 25, "TCF" should read --TCP--.

Column 21, line 19, "be(ween" should read --between--.

Column 22, line 22, "5 mol %" should read --1.5 mol %--.

Signed and Sealed this

First Day of November, 1994

*Attest:*

BRUCE LEHMAN

*Attesting Officer*  *Commissioner of Patents and Trademarks*